United States Patent [19]

Peel

[11] 3,979,407
[45] Sept. 7, 1976

[54] CHROMONE DERIVATIVES
[75] Inventor: Mervyn Evan Peel, London, England
[73] Assignee: Allen & Hanburys Limited, London, England
[22] Filed: June 29, 1971
[21] Appl. No.: 158,055

[30] Foreign Application Priority Data
July 31, 1970 United Kingdom............... 37114/70

[52] U.S. Cl.......................... 260/308 D; 260/345.2; 424/269
[51] Int. Cl.$^2$....................................... C07D 405/14
[58] Field of Search................................. 260/308 D

[56] References Cited
UNITED STATES PATENTS
3,419,578   12/1968   Fitzmaurice et al................ 424/283
3,531,493   9/1970    Gittos et al...................... 260/308 D OTHER PUBLICATIONS
Buchanan, et al., J. Med. Chem., vol. 12, pp. 1001–1006 (1969).
Juby, et al., I, J. Med. Chem., vol. 11, pp. 111–117 (1968).
Juby, et al., II, J. Med. Chem., vol. 12, pp. 396–401 (1969).
Stephens, et al., J. Am. Chem. Soc., vol. 77, pp. 1701–1702 (1955).
Mcomie, Advances In Organic Chemistry, Methods and Results, vol. 3, (Interscience Publishers, 1963), pp. 216 and 219–220.

*Primary Examiner*—Alton D. Rollins
*Attorney, Agent, or Firm*—Bacon & Thomas

[57] ABSTRACT

The compound 5,5'-[(2-hydroxytrimethylene)dioxy]bis[2(1H-tetrazol-5-yl)chromone] and non-toxic pharmaceutically acceptable salts thereof.

This compound inhibits the release of spasmogen from antibody-antigen reactions.

1 Claim, No Drawings

CHROMONE DERIVATIVES

This invention relates to a novel chromone derivative and to compositions containing the same as well as processes for the production thereof.

In application Ser. No. 116,669, filed Feb. 18, 1971 of myself and Alexander William Oxford, now abandoned, there are disclosed certain novel chromone derivatives which have interesting pharmacological activity and in particular inhibit the release of spasmogen mediators in reagin-based allergic reactions. These chromone derivatives have the general formula I:

when given intravenously is about 30 times more potent than sodium chromoglycate in inhibiting the PCA reaction in sensitised rats challenged with Nippostrongylis brasiliensis as antigen. The PCA test is described by Ogilvie (J. Immunol., 1967, 12, (2) 113).

This compound is therefore of value in the treatment of conditions in which extrinsic antigen combination with a reaginic antibody is primarily responsible, for example, extrinsic asthma, hay fever, urticaria, eczema or atopic dermatitis.

The invention therefore provides as a new compound, the compound of formula II below

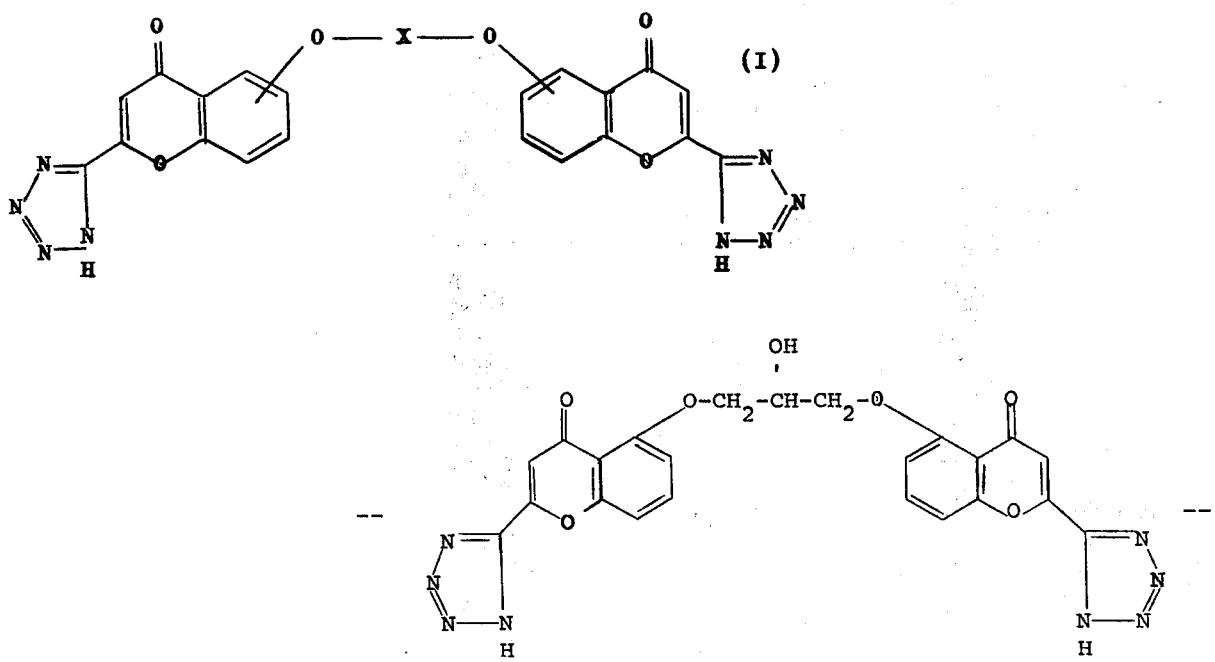

in which X is a straight or branched hydrocarbon chain containing from 2 to 6 carbon atoms which chain may optionally be substituted by one or more hydroxy radicals; and non-toxic pharmaceutically acceptable salts thereof. The salts may be those formed with inorganic bases, e.g. sodium hydroxide, potassium hydroxide, ammonium hydroxide, or those formed with organic bases, preferably with aminoalkanols, e.g. dimethylaminoethanol.

It has now been found that a particular member of this group of compounds, that is the compound in which X represents a group

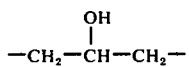

attached through the oxygen atoms to the 5,5'-positions of the molecule shows a surprisingly high pharmacological activity, more particularly of the type referred to in the said co-pending application.

The chromone derivative according to the invention has been shown to inhibit the release of spasmogens from antibody-antigen reactions such as occur in the rat during the PCA (passive cutaneous anaphylaxis test). Thus the compound according to the invention Also included in the invention are the non-toxic pharmaceutically acceptable salts of (II). The salts may be those formed with inorganic bases e.g. sodium hydroxide, ammonium hydroxide, or those formed with organic bases, for example with aminoalkanols e.g. dimethylaminoethanol.

The invention also provides pharmaceutical compositions which contain a chromone derivative I or a salt thereof, with a pharmaceutically acceptable carrier.

The pharmaceutical compositions according to the invention, may be formulated for use in the conventional manner with the aid of carriers or excipients and formulatory agents as required and with or without supplementary medicinal agents.

Oral administration is most convenient in the form of tablets which may or may not be coated, capsules, pastes, aqueous or oily suspensions, solutions or emulsions. Carriers include inert diluents such as calcium sulphate or calcium phosphate and/or disintegrating agents such as starch or alginic acid. Magnesium stearate may be used as a lubricating agent. For liquid oral formulations suspending agents such as sodium carboxymethyl cellulose may be used together with preservatives and flavouring or sweetening agents such as sucrose, dextrose and glycerol.

Injections may be formulated with the aid of physiologically acceptable carriers and agents as solutions, suspensions or as dry products for reconstruction before use.

For administration by inhalation the composition according to the invention may be conveniently in the form of an aerosol spray presentation. Such as aerosol composition may be presented in combination with a bronchodilator if required.

The dosage at which the active ingredient is administered may vary within a wide range. A suitable oral dosage range is generally from 5 to 500 mgs. In the case of an aerosol, the dosage unit may be determined by providing a metering valve in the aerosol pack so that it delivers a metered amount. Such a metered amount may be of the order of 0.1 to 10 mgs. The pharmaceutical composition may, with advantage, be formulated to provide a dose within these ranges either as a single unit or as a number of units.

The compound according to the invention may be prepared by a number of processes. The basis of most of the methods is the treatment of the corresponding nitrile of general formula IIIa, with hydrazoic acid or a salt thereof. Suitable salts of hydrazoic acid, include, for azides such as sodium azide or ammonium azide or a salt with an organic base such as aniline.

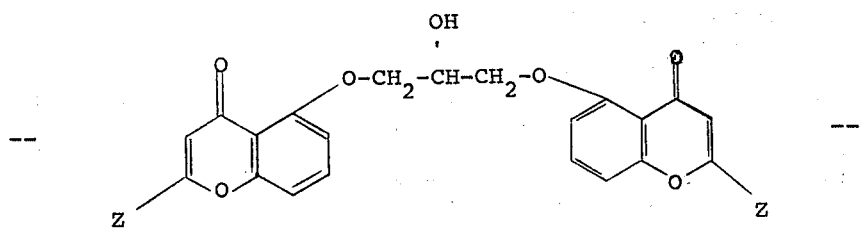

| IIIa Z = —CN | IIIc Z = —CONH₂ |
| IIIb Z = —CO₂Alk | |

The reaction is preferably effected in a solvent such as, for example, dimethyl formamide, tetrahydrofuran, dioxan, or ethyleneglycoldimethylether at an elevated temperature, for example 50°–100°C.

The nitrile may be prepared from the corresponding acid by standard routes. For example, treatment of the ester IIIb with ammonia yields the amide IIIc and dehydration of this with a suitable dehydrating agent, for example, p-toluenesulphonyl chloride in a mixture of pyridine and dimethylformamide, furnishes the nitrile IIIa. We have found that this synthetic route is particularly advantageous for the preparation of the compound according to the invention, that is where since under these reaction conditions the hydroxyl group is protected by formylation. This prevents any unwanted side reactions, e.g. dehydration, from occurring at that site. The formyl group is removed during conversion of the resulting nitrile (III), which is novel, to the tetrazole.

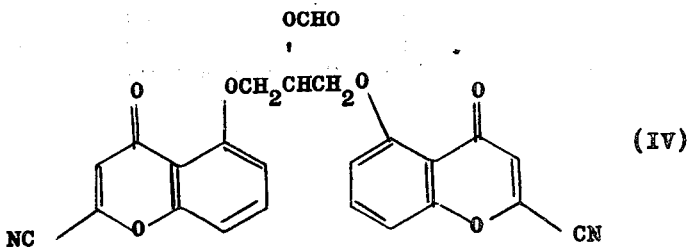

The bis ester IIIb is prepared in a manner similar to that described in United Kingdom Patent 1,144,905 and Netherlands Patent Application 6,603,997. The appropriate dihydroxy acetophenone is treated with a suitable alkylating agent, for example, epichlorohydrin or trimethylene dibromide, to give the diketone of general formula (V)

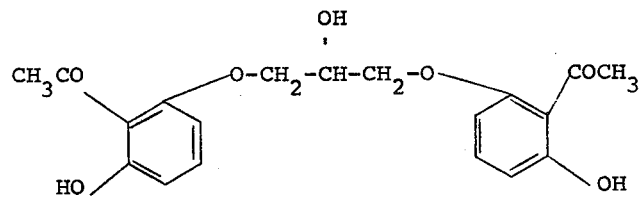

Reaction of the diketone (V) with, for example, diethyl oxalate followed by cyclisation with hydrochloric acid, then gives the required bis ester.

The following Example illustrates the invention:

EXAMPLE 5,5'-[(2-Hydroxytrimethylene)dioxy]bis[4-oxo-4H-1-benzopyran-2-carboxylic acid] diethyl ester (Brit. Pat. 1,144,905) (3.8 g) in dichloromethane (75 ml) and dry ethanol (75 ml) was cooled in ice and saturated with ammonia. 5,5'-[(2-Hydroxytrimethylene)dioxy]-bis[4-oxo-4H-1-benzopyran-2-carboxamide] separated and was collected, m.p. 278°–282°.

A mixture of the above amide (2 g) in dry pyridine (25 ml) and dry dimethylformamide (25 ml) was heated at 70° for 80 minutes with p-toluenesulphonyl chloride (5.4 g), cooled and poured into water. The precipitate was collected, dried and purified by chromatography on silica to yield the novel formate ester 5,5'-[(2-Hydroxytrimethylene)dioxy]bis[4-oxo-4H-1-benzopyran-2-carbonitrile]formate, m.p. 218°–222°.

Sodium azide (0.39 g) and ammonium chloride (0.32g) were added to the above nitrile (0.98 g) in dry dimethylformamide (15 ml) and the mixture was heated at 90° for 3 hours, and poured into water (ca 200 ml). Dilute acid was added and the mixture warmed on a steam bath to give 5,5'-[(2-Hydroxytrimethylene)dioxy]bis[2(1H-tetrazol-5-yl)chromone] trihydrate m.p. ca 212° (d) with prior softening at 189°.

I claim:

1. 5,5'-[(2-Hydroxytrimethylene)dioxy]bis[2(1H-tetrazol-5-yl)chromone] or a non-toxic pharmaceutically acceptable salt thereof.

* * * * *